United States Patent [19]

Liland et al.

[11] Patent Number: 4,612,230

[45] Date of Patent: Sep. 16, 1986

[54] SURGICAL WOUND CLOSURE TAPE

[75] Inventors: Alfred Liland, Wharton; Donald W. Regula, Flagtown, both of N.J.

[73] Assignee: Ethicon, Inc., Somerville, N.J.

[21] Appl. No.: 819,577

[22] Filed: Jan. 17, 1986

[51] Int. Cl.[4] .............................................. B32B 3/30
[52] U.S. Cl. ...................................... 428/167; 128/155; 128/156; 128/157; 428/171; 428/172; 428/343
[58] Field of Search ................. 428/40, 156, 172, 354, 428/280, 288, 289, 290, 167, 171, 296; 128/155-157

[56] References Cited

U.S. PATENT DOCUMENTS

| | | | |
|---|---|---|---|
| 3,991,754 | 11/1976 | Gertzman | 128/156 |
| 4,292,360 | 9/1981 | Riedel et al. | 428/171 |
| 4,302,500 | 11/1981 | Flora | 428/317.5 |

Primary Examiner—George F. Lesmes
Assistant Examiner—P. Schwartz
Attorney, Agent, or Firm—Robert L. Minier

[57] ABSTRACT

A wound closure tape of a substrate and a pressure sensitive adhesive. The substrate has a specific pattern of indentations which provide the tape with improved elastic properties, excellent drape and desired abrasion and tensile properties.

4 Claims, 4 Drawing Figures

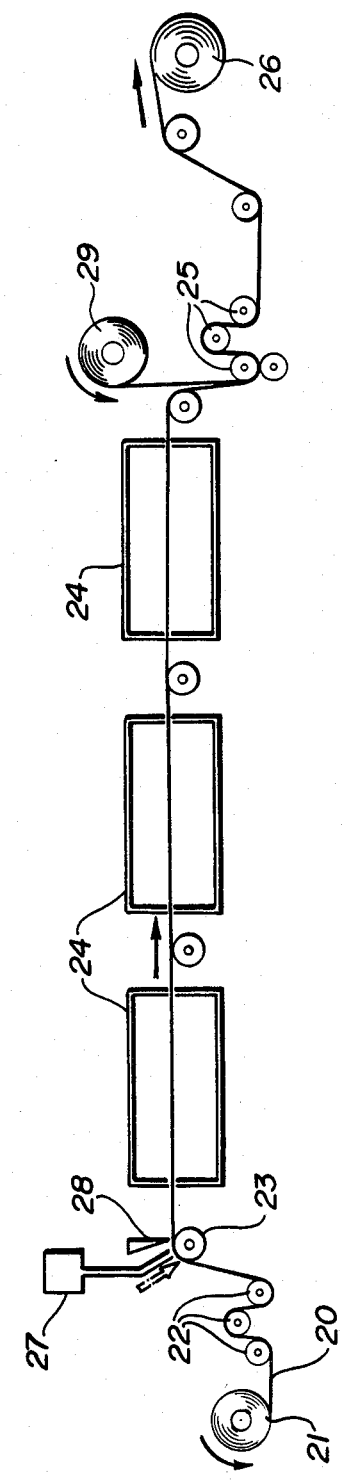

SURGICAL WOUND CLOSURE TAPE

BACKGROUND OF THE INVENTION

The present invention relates to pressure-sensitive adhesive tapes, and more particularly to surgical tapes for use in closing wounds. Pressure-sensitive adhesive tapes have been known for some time. Such tapes have gained wide acceptance for closing minor wounds or covering abrasions. In some instances, microporous or breathable, pressure-sensitive tapes have been developed and are used either to cover minor wounds or wounds that have been partially healed. Very often such tapes have been used in conjunction with sutures to close major wounds. Also in certain instances the wound is initially closed with sutures or staples which are removed a few days after surgery and the wound then supported or reinforced with surgical tape. Such a practice allows drainage of the wound and very often improves the cosmetic results of the surgery. Representative examples of such pressure-sensitive adhesive tapes are shown in U.S. Pat. Nos. 3,908,650, 3,991,754, and 4,302,500.

While such wound closure tapes have been greatly improved over the years in that they have been made of microporous materials which will allow the wound to breath and will allow water to escape from the wound and, hence, eliminate the maceration of the wound, none of these prior art tapes have gained wide acceptance for being the primary mechanism for closing major wounds. It is believed that none of these prior art tapes have gained wide acceptance as primary wound closure devices because they do not have the desired and critical combination of properties. Some of the prior art tapes have one or more of the desirable properties but to our knowledge no tape has all of the desired properties. It is believed that to be a primary wound closure tape, the tape should have good and controlled elastic recovery; that is, it must have some give or elasticity so that it will move with the tissue surrounding the wound but not such elasticity that it will allow the wound to open in any manner. The tape must also drape; that is, it must have excellent conformability to the area to which it is adhered. It is believed this is also important to maintain good wound closure. The tape should have good abrasion resistance and tear strength. The tape should also be permeable to water vapor; that is, it should be porous and breathable and not cause maceration of the wound area. The tape should have good adhesive strength and not curl at its edges.

It is an object of the present invention to provide a wound closure tape that may be used in conjunction with sutures to close wounds and also may be used as a primary closure for a wound. It is a further object of the present invention to provide a wound closure tape that has excellent drape and the required controlled elastic recovery. It is a further object of the present invention to provide a tape that will not curl at the edges. has excellent tensile and strength properties and good abrasion resistance. It is yet another object of the present invention to provide a tape that can be manufactured easily and economically. Other objects of the present invention will be readily apparent from the ensuing description and claims.

SUMMARY OF THE PRESENT INVENTION

A surgical wound closure tape suitable for use as the primary closure of a wound, said tape having a longitudinal direction and a transverse direction. The tape comprises a substrate of a nonwoven fabric. One surface of the substrate is smooth and has a pressure-sensitive adhesive mass uniformly disposed over that surface. The opposite surface of the tape has a plurality of indentations disposed over the surface. Each indentation is rectangular in shape with the length of the rectanguler being at least 5 times the width of the rectangle. The rectangles are disposed in parallel rows with the length of each rectangle extending in the transverse direction of the tape. The rectangles in adjacent rows are in overlapping relationship with each rectanguler spaced from all adjacent rectangles by a distance equal to or greater than the width of the rectangle. The described indentations provide a tape having excellent yet controlled elasticity, good drape, abrasion resistance, tear strength and a reduced propensity to curl at the edges of the tape.

The invention will be more fully described when taken in conjunction with the following drawings.

BRIEF DESCRIPTION OF THE DRAWINGS

FIG. 4 is a schematic diagram depicting one technique for producing a wound closure tape according to the present invention.

DETAILED DESCRIPTION OF THE INVENTION

Figure 1:
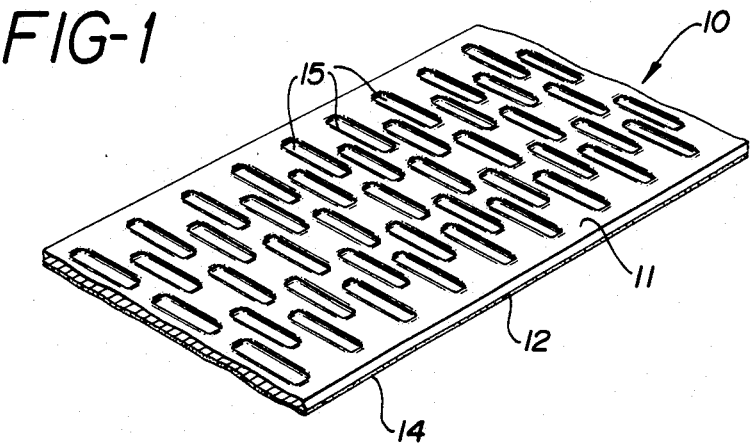
FIG. 1 is a perspective view of the new surgical wound closure tape of the present invention.
Figure 3:
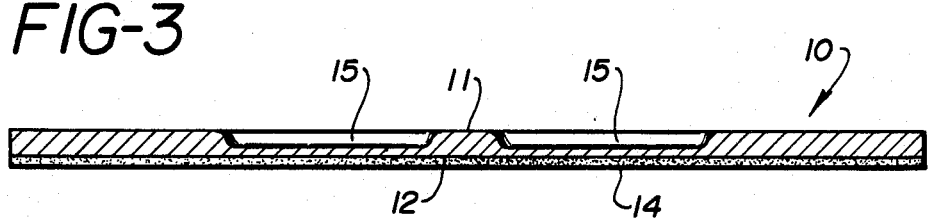
FIG. 3 is a cross-sectional view taken along line 3—3 of FIG. 2.

Referring to the drawings, in FIG. 1 there is shown the improved surgical wound closure tape 10 of the present invention. The tape comprises a substrate 11 which may be a nonwoven fabric and is preferably a spunbounded fabric. Suitable fabrics are the spunbounded fabrics made from nylon, polyester, polypropylene, and the like. These fabrics comprise continuous fibers which are disposed in a random array and which are joined at many of their cross-over points either by a binder or by heat fusing or some other bonding technique. The substrate is porous and readily allows both water vapor and air to pass through the substrate. As may be seen in FIG. 3, one surface 12 of the substrate is smooth and on that surface is a porous pressure-sensitive adhesive 14. Any of the non-toxic pressure-sensitive adhesives which are permeable to gas and water vapor may be used. Pressure-sensitive adhesives are adhesives which are inherently tacky, visco-elastic, and cohesive in the normal dry state and which are also non-toxic, non-irritating and suitable for use in surgical, dermatological or cosmetic applications. Such products are well known in the art. Some examples of representative materials suitable for use as adhesive coatings on surgical tapes are given in U.S. Pat. No. 3,645,835. Suitable examples are blends of vinyl ether, acrylic polymers, hydroxy acrylate polymers, polyethers and acrylate ester copolymers containing hydrophilic groups. Other suitable adhesives include rubber based adhesives such as polyisobutylene, and mixtures of polyisobutylene with natural rubber and the rubber copolymer of isoacrylate and acrylic acid as described in U.S. Pat. Nos. 2,884,126 and 3,121,021.

The adhesive coating should be porous and should be uniformly disposed over the smooth surface of the substrate. Generally, the adhesive coating is relatively continuous. The adhesive is preferably applied to the substrate at a level of about 40 to 100 grams per square meter. Application is conveniently accomplished by a transfer process wherein the adhesive solution is spread on a release coated paper, dried and partially cured and then contacted with the substrate with sufficient pressure to insure good bonding. The release paper is then removed and the adhesive either dried or cured, if necessary.

It should be pointed out that certain substrates, especially in dry atmospheres, will develop a static charge. Hence, when using some materials such as nylon it may be desirable to place a surface treatment on the substrate before the pressure sensitive adhesive is applied to the substrate.

Figure 2:
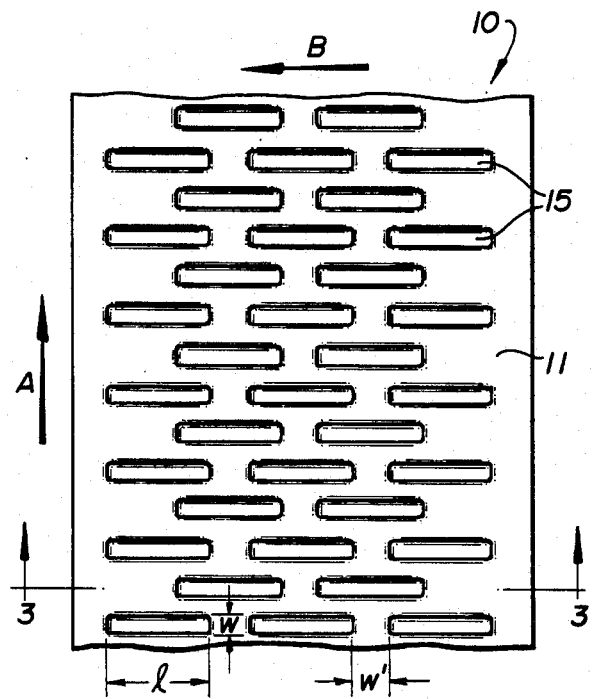
FIG. 2 is an enlarged top view depicting the pattern of indentations in the surgical wound closure tape of the present invention.

The critical part of the present invention is depicted in FIG. 2 which shows the novel surface configuration of the wound closure tape of the present invention. As will be seen in FIG. 3, the upper surface is the surface not containing the pressure-sensitive adhesive. This surface has a plurality of indentations 15 placed in it. As may be seen in FIG. 2, these indentations are rectangular in shape. The length (1) of each rectangular indentation must be at least 5 times the width (w) of the indentation. The length of the indentation runs in the transverse direction B of the tape. The indentations are disposed in adjacent parallel rows with the indentations of one row overlapping the indentations of the adjacent row. Each indentation is spaced from each adjacent indentation by at least the width (w') of an indentation The indentations are placed in the tape before coating the smooth surface of the tape with adhesive. The indentations are placed in the tape by passing the substrate through the nip formed by a heated patterned print roll which has raised areas and a heated smooth steel roll. The rolls are heated to a temperature above the glass transition temperature of the substrate and below the melting point of the substrate. When the substrate is passed between the two rolls under appropriate pressure, the filaments or fibers tend to be fused together into the pattern desired and the indentations are formed while maintaining the opposite surface smooth. The pressure-sensitive adhesive may then be placed on the smooth surface as previously described.

It is believed the above-described critical pattern of indentations placed on only one surface of the tape provides a unique and unexpected combination of properties in the resultant wound closure tape. By utilizing this pattern, the resultant tape unexpectedly requires little work to extend the tape to a low degree of extension; that is, to extend the tape 5% the work is greatly reduced over a tape not having this critical configuration of indentations. However, if it is desired to extend the tape 10% or more, my new tape unexpectedly requires greater work than the prior art tapes. This very controlled elasticity requires reduced work to attain lower extensions but increased work to attain higher extensions. The indentations also provide a tape which readily conforms to the tissue to be joined and moves with movement of the tissue yet maintains the tissue in place and held together under considerable stress. In combination with this improved elasticity and controlled elasticity, my unique wound closure tape also has increased drape; that is, it has an increased ability to conform to skin surface contours and, hence, once the strip is applied, it tends not to curl at the edges during wear.

The improved tape has good abrasion resistance because of the fusing of the filaments in the indentations and the increased density of these areas reduces the tendency for the tape to "pill". The tape also has excellent tear strength. My new tape is easy and economical to produce and process.

Many wound closure tapes are cut to a desired length and size and placed on dispensing cards. Cutting the tape can be a difficult problem. However, with my new tape, a crush slitting technique may readily be used to cut the tape. In such a technique, a gapped slitting roll cuts the tape against a smooth roll surface. The gap is set to avoid roll to roll contact and dulling of the slitting roll. The rolls must be close enough to crush the backing to the point of failure and separation. By forming the indentations in the tape, we have unexpectedly found it easier to crush cut such tapes and the tapes may be cut at high speeds with excellent yields.

The present invention is further described by the following example which is presented for purposes of illustration and comparision:

EXAMPLE

A spun bonded nylon sold under the trademark CEREX by the Monsanto Corporation is treated to from a pattern of indentations over one of its surfaces. The CEREX spunbonded nylon weighs 1 oz/sq. yd. and is passed through a pattern roll having a raised pattern of rectangles disposed over the surface of the roll. Each rectangle has a length 6 times the width of the rectangle with the length of the rectangle aligned with the roll axis. Adjacent rectangles in the same row are spaced from other rectangles in that row by twice the width of the rectangle and rectangles in one row are spaced from rectangles in an adjacent row by a distance equal to the width of a rectangle. The rectangles in adjacent rows overlap each other. The pattern roll is heated to a temperature of 182° C. and the backing roll is heated to a temperature of 185° C. A pressure of 90 lbs/sq. inch is placed at the nip between the rolls. That pressure is applied at the nip of the rolls and the CEREX spunbonded nylon substrate is passed through the nip at a speed of about 30 ft/min. to place a pattern of indentations corresponding to the pattern of the raised area rectangles on the pattern roll into one surface of the substrate. A sample of the resultant patterned substrate is tested for elastic recovery, drape, and tear strength. Along with this testing a sample of the same substrate which has not been treated in accordance with the present invention and has no pattern of indentations is also tested by the same techniques for elastic recovery, drape and tear strength. The elastic properties of strips of both the treated and untreated tape cut in the machine direction are tested in accordance with Procedure A of ASTM/D 1774-79 Elastic Properties of Textile Fibers. The test is conducted on an Instron Tensile Tester Model #1132. The only modification to the test are that the specimen tested is ¼ inch by 3 inches and the gauge length is reduced to 2 centimeters. A patterned tape at 2% extension requires 16,890 dynes cm. to obtain that extension. The tape at that extension is deformed 11% and has 89% of its tensile strength remaining. The patterned tape at a 5% extension requires 36,267 dynes cm. to extend it that degree. The tape is deformed 13% and has 87% of its tensile strength remaining while the patterned tape when extended 10% requires 142,880 dynes cm. to extend it 10%. It has a deformation of 24% and retains 76% of its tensile strength.

Contrasted to this, the untreated product requires 28,815 dynes cm. to extend it 2%, 42,527 dynes cm. to extend it 5%, and 128,275 dynes cm. to extend it 10%. The untreated tape has the same degree of deformation and retains about the same percent of tensile strength as the patterned tape. Hence, as may be seen, while my new tape is not deformed any more and retains the desired degree of tensile strength, it does require less work to extend it up to 5% but considerably more work to extend it to 10%.

Similar samples of the tape are tested for drape. The drape test is a relatively simple test and a length of the tape is hung over the edge of a plexiglass member ½ inch thick, in an unsupported state and the degree of deflection measured. The sample size used is ¼ inch by 3 inches or ½ inch by 4 inches. In the patterned tape, when a 1 inch length is hung over a member, the angle is 16° while with the untreated tape it is only 0.2°. When the length is increased to 1½ inches, the angle of the patterned tape increases to 30° and the untreated tape is only 10° and if a 2 inch length is hung over the member, the angle of the patterned tape increases to 45° while the untreated tape increases to 34°. This clearly shows greatly improved drape characteristics in the patterned tape of the present invention.

The tear strength of samples of treated and untreated tape are also determined. The tear strength measurements are performed in both the machine and transverse directions in accordance with ASTM/D 1004.66 Initial Tear Resistance of Plastic Film and Sheeting. The machine direction tear strength of the patterned tape is 2.8 while the transverse direction tear strength is 3.3. Compared to this, the machine direction tear strength of the untreated tape is 3.8 and the transverse direction tear strength 2.8. There is no significant change in the tear strength of the tapes.

The patterned substrate is coated with a pressure-sensitive adhesive which is spread on a release paper at a level of about 50 grams per sq. meter and the substrate embedded in that adhesive with the smooth surface contacting the adhesive.

To coat the tape with a pressure sensitive adhesive, a line, as schematically shown in FIG. 4, is strung with a release paper 20. The paper is taken from a feed roll 21, passed through tensioning roller guides 22, then over an adhesive supply roll 23, through curing ovens 24 to laminating roller 25 and finally to a bulk roll wind-up. As the release paper passes over roll 23 the adhesive is foamed using an Oakes foaming unit 27 to a density of about 30 lbs/per square foot and spread on the release paper. A knife edge 28 is adjusted to provide the desired thickness of adhesive and amount of adhesive. The adhesive and release paper pass through curing ovens held at temperatures of from about 100° F. to 215° F. to slowly evaporate solvent from the adhesive. The adhesive "tack" properties are monitored to ensure a bond with the backing substrate. The backing substrate 27 is applied to the surface of the adhesive with the smooth surface of the backing substrate contacting the adhesive. The release paper, adhesive and backing substrate pass through laminating rolls 25 and the laminate wound on a wind-up roll 26. The laminate is then slit, cut and packaged as is well known in the art to produce the desired wound closure tape.

While a specific embodiment of a surgical wound closure tape has been disclosed herein, it is obvious that various changes and modifications may be made without departing from the spirit and scope of the present invention.

What is claimed is:

1. A surgical wound closure tape, said tape having a longitudinal direction and a transverse direction, said tape comprising a substrate of a nonwoven fabric, one surface of said substrate being smooth and having a pressure-sensitive adhesive uniformly disposed over said smooth surface, the opposite surface of said substrate having a plurality of indentations disposed over said surface, each indentation being rectangular in shape, each said rectangle having a length of at least 5 times the width of said rectangle, said rectangles being disposed in parallel rows with the length of each rectangle extending in the transverse direction of the tape, the rectangles in adjacent rows being in overlapping relationship with each rectangle spaced from all adjacent rectangles by a distance equal to or greater than the width of the rectangle whereby said tape has good elasticity, drape, abrasion resistance, tensile strength, and a reduced propensity to curl at the edges of the tape.

2. A surgical wound closure tape in accordance with claim 1 wherein the substrate is a spunbonded nonwoven fabric.

3. A surgical tape in accordance with claim 2 wherein the spunbonded fabric comprises randomly disposed nylon filaments.

4. A surgical wound closure tape according to claim 1 wherein the length of each rectangle is 6 times the width of the rectangle.

* * * * *